United States Patent [19]

Ambrosius et al.

[11] Patent Number: 5,578,710
[45] Date of Patent: Nov. 26, 1996

[54] ACTIVATION OF RECOMBINANT PROTEINS

[75] Inventors: Dorothea Ambrosius, Iffeldorf; Carola Dony, Starnberg; Rainer Rudolph, Weilheim, all of Germany

[73] Assignee: Boehringer Mannheim GmbH, Germany

[21] Appl. No.: 139,054

[22] Filed: Oct. 21, 1993

Related U.S. Application Data

[63] Continuation of Ser. No. 837,779, Feb. 14, 1992, abandoned.

[30] Foreign Application Priority Data

Feb. 21, 1991 [DE] Germany ............ 41 05 480.6

[51] Int. Cl.$^6$ ............ A23J 1/00; C07K 1/00; C12P 21/06
[52] U.S. Cl. ............ 530/412; 435/69.1; 435/69.5; 435/69.51; 435/69.52; 530/351
[58] Field of Search ............ 435/68.7, 68.8, 435/68.9, 69.1; 530/412, 351

[56] References Cited

U.S. PATENT DOCUMENTS

| | | | |
|---|---|---|---|
| 4,530,787 | 7/1985 | Shaked et al. | 530/363 |
| 4,783,415 | 11/1988 | Hoshiko et al. | 435/69.8 |
| 4,948,729 | 8/1990 | Piatak, Jr. et al. | 435/172.1 |
| 5,013,653 | 5/1991 | Huston et al. | 435/69.7 |
| 5,043,156 | 8/1991 | Matsumoto et al. | 424/85.1 |
| 5,077,392 | 12/1991 | Rudolph et al. | 435/219 |
| 5,082,775 | 1/1992 | McCaman et al. | 435/69.7 |
| 5,087,564 | 2/1992 | Mai et al. | 435/69.7 |
| 5,115,102 | 5/1992 | Haymore et al. | 530/350 |
| 5,191,063 | 3/1993 | Inouye et al. | 530/324 |

FOREIGN PATENT DOCUMENTS 389034  9/1990  European Pat. Off.

OTHER PUBLICATIONS

Mulks et al. "Relationship Between the Specificity of IgA Proteases and Serotypes in Haemophilus influenzae", Journal of Infectious Diseases, vol. 146, No. 2, Aug. 1982, pp. 265–274.

Mulks et al. (1980) Jour. Exp. Med. vol. 152 pp. 1442–1447.

*Primary Examiner*—Robert A. Wax
*Assistant Examiner*—Hyosuk Kim
*Attorney, Agent, or Firm*—Nikaido, Marmelstein, Murray & Oram LLP

[57]  ABSTRACT

A process for the activation of recombinant proteins which are present in at least a partially inactive form in which a protein is activated by known solubilization or/and renaturation techniques, said protein having additional helper sequences 2 to 50 amino acids in length at its N- or/and C-terminus whereby the relative hydrophobicity of these helper sequences which is calculated as the sum of the relative hydrophobicity specified in Table 1 for the individual amino acids has a negative numerical value.

14 Claims, 4 Drawing Sheets

ACTIVATION OF RECOMBINANT PROTEINS

This application is a continuation division of application Ser. No. 07/837,779 filed Feb. 14, 1992, now abandoned.

The present invention concerns a process for the activation of recombinant proteins, in particular for the activation of recombinant proteins from prokaryotes.

When recombinant proteins are expressed in prokaryotes the proteins are often produced in the host cell in the form of at least partially inactive, sparingly soluble aggregates (refractile bodies, inclusion bodies IB) which furthermore may also be contaminated with proteins of the host cell. Before such proteins can be used, for example for therapeutic or diagnostic purposes, they must be converted into their active form.

Processes for the renaturation of recombinant proteins are generally known and disclosed for example in EP-A 0 114 506, WO 86/00610, WO 84/03711, U.S. Pat. No. 4,530,787 and in EP-A 0 241 022. However, when activating natural protein sequences low yields are often obtained with these known methods. The underlying object of the present invention is therefore to achieve an improvement in the renaturation yields of recombinant proteins. In principle it would have been possible to achieve this by providing a process in which the yields are improved by selection of renaturation conditions. This is, however, not the subject matter of the present invention.

The achievement of the object according to the present invention is based on the surprising observation that the renaturation yield of a protein is increased when additional helper sequences are added to its N- or/and C-terminus.

The present invention therefore provides a process for the activation of recombinant proteins, in particular of recombinant proteins from prokaryotes which are present in at least a partially inactive form, whereby this process is characterized in that a protein is activated by known solubilization or/and renaturation techniques, said protein having additional helper sequences 2 to 50 amino acids in length at its N- or/and C-terminus whereby the relative hydrophobicities of these helper sequences, which are calculated as the sum of the relative hydrophobicities specified in Table 1 for the individual amino acids, has a negative numerical value.

The term "relative hydrophobicity" as used within the sense of the present invention is derived from the citations T. E. Creighton (1983), Proteins, Structure and Molecular Principles, W. H. Freeman and Company, New York, p. 142, Table 4.4; G. yon Heijne and C. Blomberg (1979) Eur. J. Biochem. 95, 175–181 and Y. Nozaki and C. Tanford (1971), J. Biol. Chem. 246, 2211–2217. The value for the relative hydrophobicity of an amino acid is determined e.g. according to Nozaki/Tanford by determination of the partition equilibrium of this amino acid between a non-polar solvent (e.g. ethanol/dioxan) and water. The relative hydrophobicity is an energy quantity and is thus stated in kcal/mol. A positive value for the relative hydrophobicity means that there is a preference for non-polar solvents, i.e. that it is a non-polar amino acid. If in contrast the relative hydrophobicity has a numerical value which is smaller than 0 then it is a polar amino acid which has a preference for water compared to a non-polar solvent. As a consequence energy is released when such an amino acid is transferred for example from ethanol to water.

The values for the relative hydrophobicity of the individual amino acids are compiled in the following Table 1.

TABLE 1

| Amino acids | Relative hydrophobicity (kcal/mol) |
|---|---|
| Gly | 0 |
| Leu | 1.8 |
| Ile | 2.5 |
| Val | 1.5 |
| Ala | 0.5 |
| Phe | 2.5 |
| Cys | −2.8 |
| Met | 1.3 |
| Thr | 0.4 |
| Ser | −0.3 |
| Trp | 3.4 |
| Tyr | 2.3 |
| Gln | −0.3 |
| Lys | −4.2 |
| Asn | −0.2 |
| Glu | −9.9 |
| His | 0.5 |
| Asp | −7.4 |
| Arg | −11.2 |
| Pro | −3.3 |

It is apparent from this table that the amino acids cysteine, proline and in particular glutamate, aspartate, arginine and lysine have a high negative relative hydrophobicity.

It was surprisingly found that the activation of recombinant proteins is considerably improved by adding helper sequences 2 to 50 amino acids in length to a protein sequence if these helper sequences have a total relative hydrophobicity which is negative. The length of these helper sequences is preferably 2 to 20, particularly preferably 5 to 20 amino acids.

In addition it is preferred that the quotients for these helper sequences of relative hydrophobicity to the number of amino acids is—2.0 kcal/mol or less, particularly preferably—2.5 kcal/mol or less and most preferably—2.8 kcal/mol or less.

The addition of helper sequences to the recombinant protein can be carried out by means of the usual techniques in the area of molecular biology. This is preferably carried out by adding an oligonucleotide sequence to one or both ends of the DNA sequence coding for a recombinant protein to be expressed, which oligonucleotide codes for one of the protein helper sequences described above with a negative relative hydrophobicity. For this purpose DNA fragments which contain a region which codes for the beginning or for the end of the corresponding gene are for example isolated from the gene to be expressed. Synthetic oligonucleotides which contain regions coding for the helper sequences can then be inserted into these DNA fragments e.g. by using other restriction cleavage sites. Another possibility is to completely replace the natural DNA fragments from the gene by oligonucleotide sequences. Modified DNA sequences can be obtained in this way which contain the information for the added helper sequences in addition to the information for a recombinant protein.

It is expedient to use DNA sequences whose codon usage is adapted to the expression organism (E. L. Winnacker, Gene und Klone, Verlag Chemie, 1985, 224–241) as DNA sequences which code for the N-terminal helper sequences.

In this case when *E. coli* is the expression organism the following codons are preferred for the following amino acids:

| | |
|---|---|
| threonine | ACA |
| proline | CCA |
| leucine | CTA |
| lysine | AAA |
| alanine | GCC |
| glutamic acid | GAA |

A DNA modified in this way which codes for a recombinant protein with added helper sequences is introduced by transformation into a host cell, preferably into a prokaryotic cell, particularly preferably into an *E. coli* cell. Subsequently the transformed cells are cultured in a suitable medium, the cells are lysed and the recombinant protein which forms in an at least partially inactive state and in particular is present in the form of inclusion bodies, is isolated. Subsequently this protein is solubilized and renatured, preferably at a pH at which the protein can take up its native conformation. These steps in the procedure can be carried out according to techniques which are already known such as for example those which are quoted in the state of the art referred to in the introduction to the description. The activation of the protein is preferably carried out by means of a pulse renaturation such as that disclosed for example in EP-A 0 241 022. The improvement of the known procedures achieved by the present invention is based in particular on the presence of helper sequences which are added to the N- or/and C-terminus of the recombinant protein. In these procedures the helper sequences are preferably added to the N-terminus of the protein to be activated. However, the attachment of helper sequences to the C-terminus also produces positive results.

Preferred helper sequences are those which contain at least 2 amino acids selected from the group comprising glutamate, aspartate, lysine, arginine and proline, whereby lysine and glutamate residues are particularly preferred and glutamate residues are the most preferred. In addition it is particularly preferred that the helper sequences contain two of the afore-mentioned charged amino acids (i.e. glutamate, aspartate, lysine and arginine) in succession each having the same charge, preferably two successive lysine or glutamate residues, especially preferably two successive glutamate residues.

If the recombinant proteins produced by the process according to the present invention are later to be used therapeutically, it is advantageous that they have a cleavage site at the junction between the helper sequences and the desired protein. By this means the protein can be obtained with its natural amino acid sequence. This cleavage site can be a sequence which is recognized by a protease or by a chemical cleavage reagent for proteins (e.g. CNBr), whereby a protease cleavage site is preferred. It is particularly preferred that the cleavage site is an IgA protease cleavage site such as that described in WO 91/11520. The exact cleavage conditions are also specified in WO 91/11520. In addition a cleavage site which is a cleavage site for factor Xa is also preferred.

Such a cleavage site in the protein sequence is not necessary when using the recombinant protein for analytical purposes.

Concrete examples of helper sequences which are suitable for improving protein activation are the following sequences added to the N-terminus of a protein:

| | |
|---|---|
| Met—Glu | (SEQ ID NO: 1) |
| Met—Thr—Pro—Leu—Pro—Arg—Pro—Pro | (SEQ ID NO: 2) |
| Met—Thr—Pro—Leu—His—His—Pro—Arg—Pro—Pro | (SEQ ID NO: 3) |
| Met—Thr—Pro—Leu—Lys—Lys—Pro—Arg—Pro—Pro | (SEQ ID NO: 4) |
| Met—Thr—Pro—Leu—Glu—Glu—Gly—Pro—Arg—Pro—Pro | (SEQ ID NO: 5) |
| Met—Thr—Pro—Leu—Glu—Glu—Gly—Thr—Pro—Leu—Pro—Arg—Pro—Pro | (SEQ ID NO: 6) |
| Met—Thr—Pro—Leu—Glu—Glu—Gln—Pro—Pro | (SEQ ID NO: 7) |
| Met—Lys—Ala—Lys—Arg—Phe—Lys—Lys—His—Pro—Arg—Pro—Pro | (SEQ ID NO: 8) |
| Met—Thr—Pro—Leu—Glu—Glu—Gly—Ile—Glu—Gly—Arg | (SEQ ID NO: 9) |
| Met—Thr—Pro—Leu—Lys—Ala—Lys—Arg—Phe—Lys—Lys—His—Pro—Arg—Pro—Pro | (SEQ ID NO: 10) |

The helper sequences SEQ ID NO: 5, 6, 7 and 9 which have two successive glutamate residues result in the highest renaturation yields and are therefore the most preferred.

The process according to the present invention is especially suitable for the activation of recombinant human proteins and their derivatives produced in prokaryotes, such as e.g. plasminogen activators, interferons, interleukins and granulocyte colony stimulating factors. It is particularly preferred that the protein to be activated is a granulocyte colony stimulating factor (G-CSF) which has the initial DNA sequence ACACCA. Derivatives of G-CSF which are disclosed in EP-A 0 456 200 are also preferred.

The vector pKK177-3-G-CSF Bg was deposited under the number DSM 5867 at the Deutsche Sammlung Für Mikroorganismen, Grisebachstr. 8, D-3400 Göttingen.

It is intended to elucidate the invention further by the following examples and figures.

EXAMPLE 1

Construction of the vectors

The vector pKK177-3 G-CSF Bg (DSM 5867) is digested with EcoRI (partially) and ApaI and the oligonucleotide (SEQ ID NO:11) and (SEQ ID NO:12)

```
EcoRI                              ApaI
    AATTCGGAGGAAAAATTA  |ATG...|ACACCACTGGGCC
                       |Met...|G-CSF sequence
                               without ATG
``` is inserted into the linearized vector fragment (ca. 3450 bp) which formed.

AATTCGGAGGAAAAATTA:        SEQ ID NO: 11

ACACCACTGGGCC:             SEQ ID NO: 12

Each of the DNA sequences used in the gap conforms with the genetic code for the amino acids listed in Table 2 i.e. an oligonucleotide with the genetic code for Met-Thr-Pro-Leu-Pro-Arg-Pro-Pro (SEQ ID NO: 3) was for example used for construct (3). The plasmids resulting from ligation of the oligonucleotides into the cleaved vector are transformed into *E. coli* HB101. In order to ensure a better regulation of the tac promoter, the cells were additionally transformed with a plasmid compatible with pBP010 (preparation cf. European Patent application No. 91 111 155.7) which contains the lacI$^q$ gene. The lacI$^q$ gene has been known for a long time to one skilled in the art and is easily obtainable. Examples of suitable plasmids which are compatible with pBP010 are e.g. pACYC 177 (DSM 3693P) into which the lacI$^q$ gene is inserted or plasmids derived therefrom (cf. e.g. Gene 85 (1989), 109–114 and EP-A 0 373 365). The resulting clones are selected on kanamycin (50 μg/ml)/ampicillin (50 μg/ml) and identified by means of restriction analysis. When cleaved with EcoRI and EcoRV fragments result with lengths of ca. 3.15 kb, ca. 0.3 kb (with the respective constructs) and 4.85 kb.

EXAMPLE 2 a) Fermentation:

Clones which were identified as positive according to Example 1 are grown in 5 ml culture in LB medium containing kanamycin and ampicillin (for concentrations see Example 1) up to an OD$_{550}$ of 0.5, induced with 5 mmol/l IPTG and incubated for 3 hours at 37° C. 10 OD of this induced culture is harvested and a total cell extract is prepared from this. The total cell extract is analyzed on a SDS page gel.

When it is apparent from this that the desired protein is being expressed, the culture is repeated on a 1 l scale, the cells are harvested and an IB preparation is carried out.

b) IB preparation:

The cells are harvested by centrifugation, taken up in 100 ml Tris magnesium buffer (10 mmol/l Tris, pH 8.0, 1 mmol/l MgCl$_2$) and lysed with lysozyme (0.3 mg/ml).

They are incubated for 15 minutes at 37° C. and subjected to one passage of a French press (1200 psi).

Subsequently a DNAse digestion (2 mg DNAse I) is carried out for 30 minutes at 37° C.

20 ml 0.5 mol/l NaCl, 20 mmol/l EDTA, pH 8.0 and 3 ml 20% Triton×100 is added and incubated for 10 minutes at room temperature.

The suspension is centrifuged for 10 minutes at 15000 rpm at 4° C. The pellet is taken up in 30 ml 50 mmol/l Tris, pH 8.0, 50 mmol/l EDTA and 0.5% Triton×100 and treated with ultrasound. It is centrifuged again, resuspended and treated with ultrasound. This procedure is repeated twice again. Subsequently it is centrifuged and the pellets obtained in this way are used as IBs in Example 3.

EXAMPLE 3

Solubilization/renaturation a) Solubilization

Solubilization buffer:

6 mol/l guanidine hydrochloride 0.1 mol/l Tris buffer, pH 8.0

1 mmol/l EDTA 100 mmol/l DTE (dithioerythreitiol)

Dialysis buffer 1:

6 mol/l guanidine hydrochloride 3 mmol/l EDTA at pH 3.0 1 g inclusion bodies is added to 30 ml solubilization buffer, homogenized for 5 minutes with ultrasound and incubated for 1 hour at room temperature. HCl is added until the pH reaches 3.0. Insoluble material is subsequently removed by centrifugation.

It is dialyzed against dialysis buffer 1 until the DTE is completely removed (≦1 mmol/l DTE).

b) Pulse reactivation:

Renaturation buffer:

0.8 mol/l arginine hydrochloride 0.1 mol/l Tris buffer, pH 8.0

0.5 mmol/l GSH 0.5 mmol/l GSSG 1 mmol/l EDTA

Dialysis buffer 2:

10 mmol/l Tris buffer, pH 8.0

1 mmol/l EDTA

The pulse reactivation is carried out as described in EP-A 0 241 022. A device according to FIG. 5 of EP-A 0 241 022 is used.

For this protein is added to the reaction volume (100 ml renaturation buffer) at intervals of 30 minutes so that the protein concentration in the reaction volume increases by 50 μg/ml per pulse. Altogether it is pulsed 20 times (final concentration ca. 1 mg/ml reaction volume).

After the pulse reactivation turbidities are removed from the reaction volume by centrifugation and the total reaction volume is dialyzed against dialysis buffer 2 until arginine has been removed (≦50 mmol/l). (It is expedient to check this by measuring the conductivity. The dialysis can be finished when the conductivities of dialysis buffer and reaction volume are identical.) The reactivation yields for the individual constructs which were determined by means of an activity test are shown in Table 2.

TABLE 2

|  | % Renaturation[2] | Relative hydrophobicity (kcal/mol) | rel. hydrophobicity number of amino acids |
|---|---|---|---|
| (0) Met—G-CSF[1] | 10 | 1,3 | 1,3 |
| (1) Met—Glu—G-CSF | 50 | −8,6 | −4,3 |
| (2) Met—Thr—Pro—Leu—Pro—Arg—Pro—Pro—G-CSF | 20 | −20,9 | −2,6 |
| (3) Met—Thr—Pro—Leu—His—His—Pro—Arg—Pro—Pro—G-CSF | 20 | −19,9 | −2 |
| (4) Met—Thr—Pro—Leu—Lys—Lys—Pro—Arg—Pro—Pro—G-CSF | 50 | −29,3 | −2,9 |
| (5) Met—Thr—Pro—Leu—Glu—Glu—Gly—Pro—Arg—Pro—Pro—G-CSF | 80–90 | −40,7 | −3,7 |
| (6) Met—Thr—Pro—Leu—Glu—Glu—Gly—Thr—Pro—Leu—Pro—Arg—Pro—Pro—G-CSF | 80 | −41,8 | −2,9 |
| (7) Met—Thr—Pro—Leu—Glu—Glu—Gln—Pro—Pro—G-CSF | 80 | −26,5 | −2,9 |
| (8) Met—Lys—Ala—Lys—Arg—Phe—Lys—Lys—His—Pro—Arg—Pro—Pro—G-CSF | 60 | −44,3 | −3,4 |
| (9) Met—Thr—Pro—Leu—Glu—Glu—Gly—Ile—Glu—Gly—Arg—G-CSF | 80 | −38,1 | −3,5 |
| (10) Met—Thr—Pro—Leu—Lys—Ala—Lys—Arg—Phe—Lys—Lys—His—Pro—Arg—Pro—Pro—G-CSF | 50 | −45,4 | −2,8 |

[1]not an example according to the present invention
[2]determined with the G-CSF activity test according to Example 3
(1) to (10): SEQ ID NO: 1 to 10 bound to the G-CSF sequence without an N-terminal methionine residue

EXAMPLE 4

Determination of the G-CSF activity

The activity of G-CSF is tested as described Biochem. J. 253 (1988) 213–218, Exp. Hematol. 17 (1989) 116–119, Proc. Natl. Acad. Sci. U.S.A. 83 (1986) 5010, using the murine leukemia line NFS60 which is completely dependent on G-CSF. The medium (RPMI medium, Boehringer Mannheim GmbH, Order No. 2099445 with 10% foetal calf serum) of the maintenance culture permanently contains 1000 U/ml G-CSF to preserve the factor dependency of the cells.

This test directly measures the G-CSF-stimulated proliferation of NFS60 cells by means of the incorporation of $^3$H-thymidine. The test is carried out in the following manner:

NFS60 cells which are in the exponential growth phase (cell density is at most $1\times10^5$ cells/ml) are transferred to microtitre plates ($1\times10^4$ cells/well) and cultured with a decreasing G-CSF concentration. The maximum dose of G-CSF in well 1 corresponds to the concentration in the maintenance culture (1000 U/ml, specific activity $1\times10^8$ U/mg protein). The dilution steps are by factors of ten.

After an incubation of about 24 hours, $^3$H-thymidine (0.1 μCi/well) is added. After this the cells are incubated for a further 16 hours.

In order to evaluate the test the cells are frozen in the microtitre plate in order to lyse them. The cell lysate is aspirated on a glass fibre filter, rinsed, dried and measured in a scintillation counter. The incorporation of $^3$H-thymidine is proportional to the G-CSF-induced proliferation of the NFS60 cells.

EXAMPLE 5

Determination of the dependence of renaturation yield on the concentration of denatured protein after a single addition.

Starting material: inclusion bodies having the constructs No. 0/3/5 and 8 of Table 2.
Solubilization and first dialysis:

The IB material is solubilized according to Example 3, dialyzed to remove the reducing agent and subsequently adjusted to a protein concentration of 30 mg/ml (M. M. Bradford, Anal. Biochem. 72 (1976) 255).

Renaturation:

The reactivation is carried out in 0.8 mol/l or 0.2 mol/l arginine hydrochloride, 10 mmol/l EDTA, 0.5 mmol/l GSH and 0.5 mmol/l GSSG at 20° C. and pH 8.0.

The protein concentrations in the respective renaturation preparations were adjusted to between 0.3 and 3 mg/ml. The concentration of guanidine hydrochloride was 0.55 mol/l in all the preparations.

After an incubation of 3 hours at room temperature the reaction was stopped by acidification (pH 4.5).

The ratio of denatured to renatured protein was determined by HPLC.

Mobile buffer A: 0.12% (v/v) trifluoroacetic acid

Mobile buffer B: 90% (v/v) acetonitrile, 0.1% (v/v) trifluoroacetic acid

Gradient of B: 40 to 70% in 30 min

Figure 1:
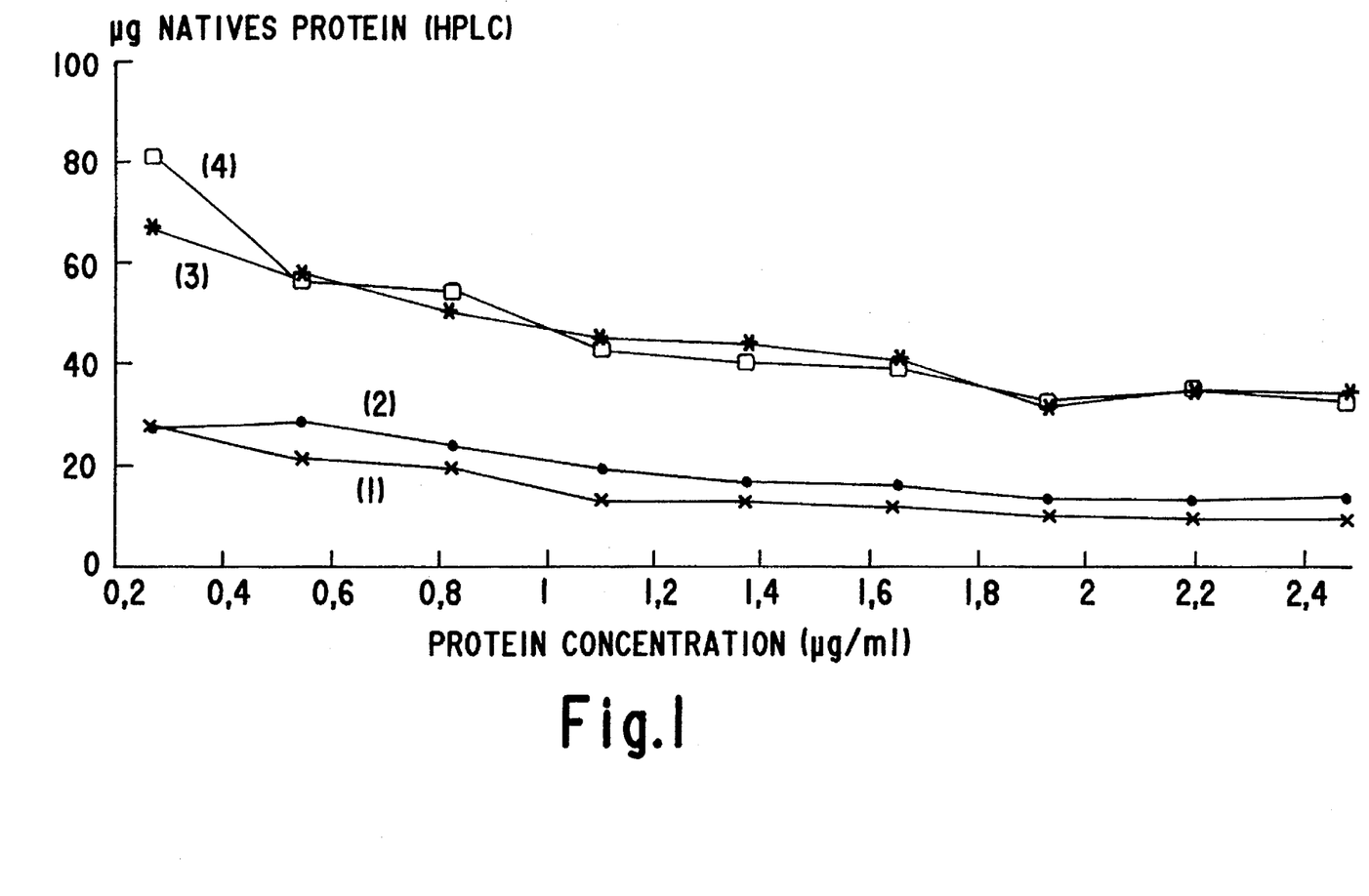
FIG. 1 shows the dependence of the renaturation yield on the concentration (arginine concentration 0.2 mol/l) for constructs which contain sequences corresponding to sequence 0 of table 2 (curve 1), SEQ ID NO:3 (curve 2), SEQ ID NO:5 (curve 3) and SEQ ID NO:8 (curve 4).
Figure 2:
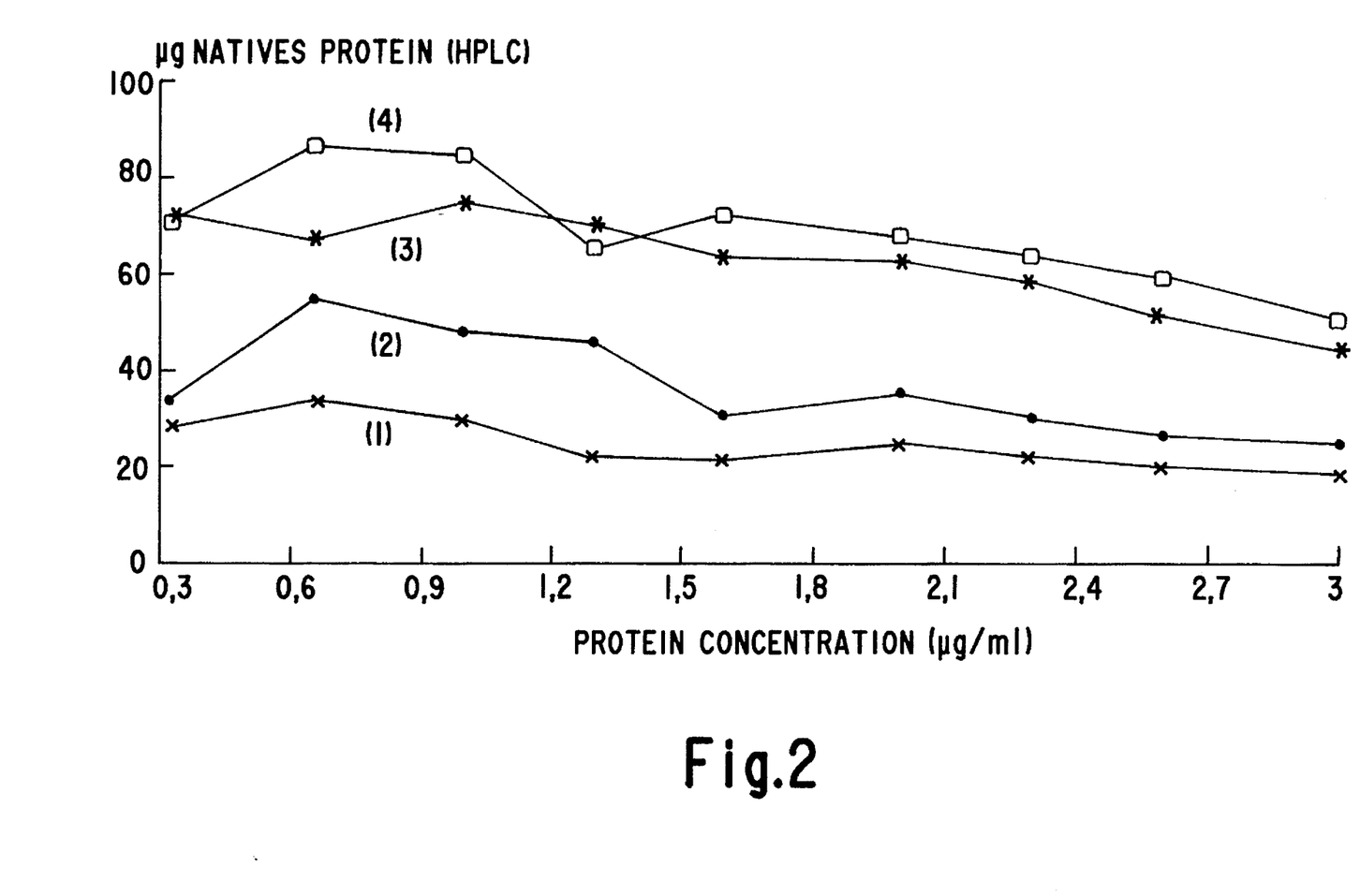
FIG. 2 shows the dependence of the renaturation yield on the concentration (arginine concentration 0.8 mol/l) for constructs which contain sequences corresponding to sequence 0 of table 2 (curve 1), SEQ ID NO:3 (curve 2), SEQ ID NO:5 (curve 3) and SEQ ID NO:8 (curve 4).

Flow rate: 1 ml/min, detection at 280 nm
The results are shown in FIG. 1 and 2.

EXAMPLE 6

Dependence of the renaturation on the arginine concentration

Dialyzed solubilizates (protein concentration 10 mg/ml) of the constructions 0,3,5 and 8 (Tab. 2) which were prepared analogously to Example 5 served as the starting material.

The protein concentration in the renaturation buffer (0 to 0.8 mol/l arginine hydrochloride, 100 mmol/l Tris, 10 mmol/l EDTA, 0.5 mmol/l GSH, 0.5 mmol/l GSSG, room temperature at pH 8) was adjusted to 1 mg/ml by a single addition of denatured protein.

After an incubation period of 3 h the reaction was stopped by acidification (pH 4.5). The subsequent evaluation was carried out by HPLC analogous to Example 5.

Figure 3:
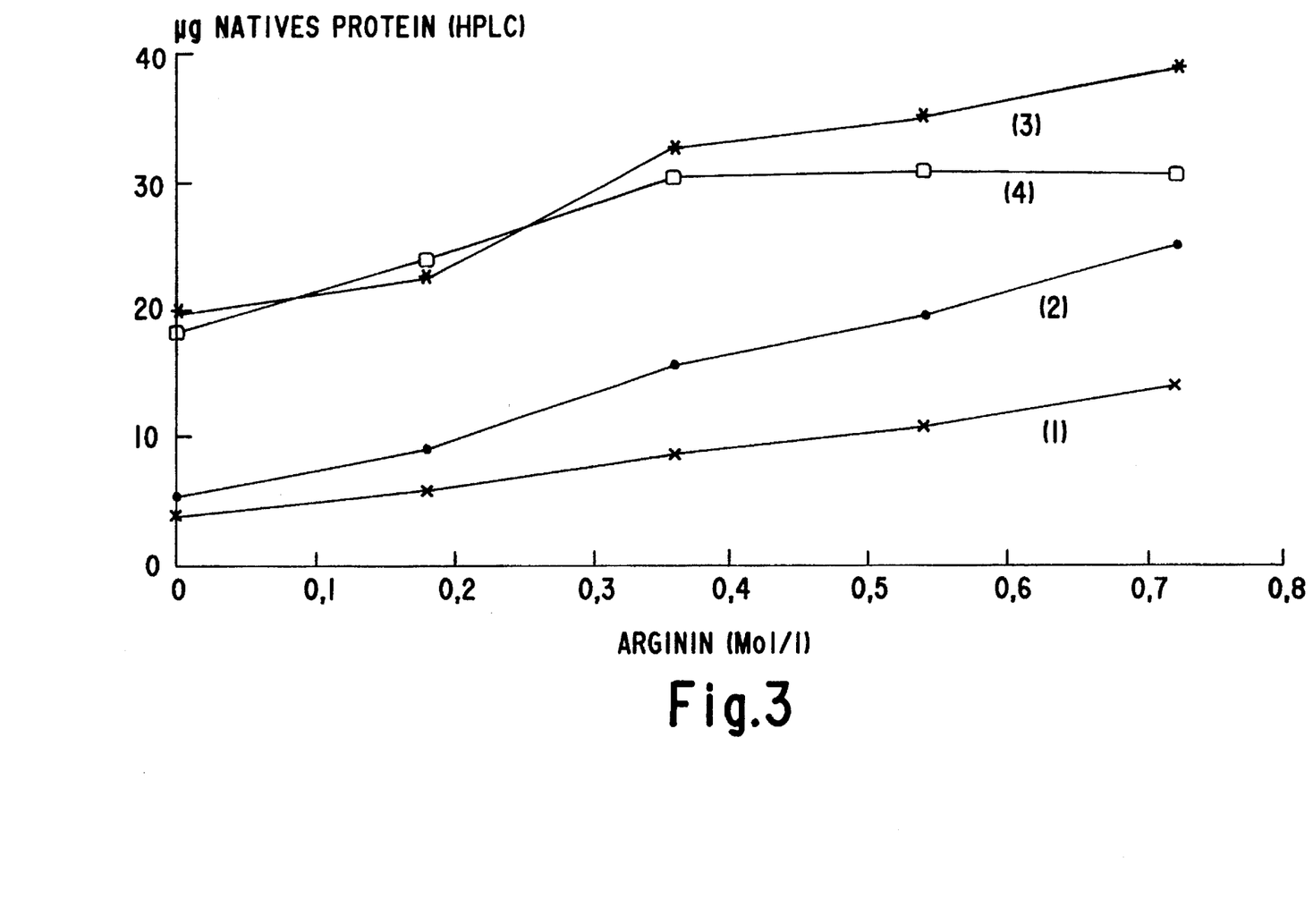
FIG. 3 shows the dependence of the renaturation yield on the arginine concentration (curve nomenclature is analogous to FIGS. 1 and 2).

The results are shown in FIG. 3.

EXAMPLE 7

Kinetics of the reactivation in 0.2 mol/l arginine buffer
Starting material: the solubilisates of Example 6 were used.

The reactivation was carried out in 0.2 mol/l arginine hydrochloride, 100 mmol/l Tris, 10 mmol/l EDTA, 0.5 mmol/l GSH, 0.5 mmol/l GSSG, at room temperature and pH 8. The protein concentration in the reaction preparation was adjusted by a single addition to 1 mg/ml and the guanidine concentration was adjusted to 0.55 mol/l. Samples were taken at 5, 10, 15, 60 and 180 minutes, the reaction was stopped in each case by acidification (pH 4.5) and subsequently the reactivation kinetics were determined by HPLC (cf. Example 5).

Figure 4:
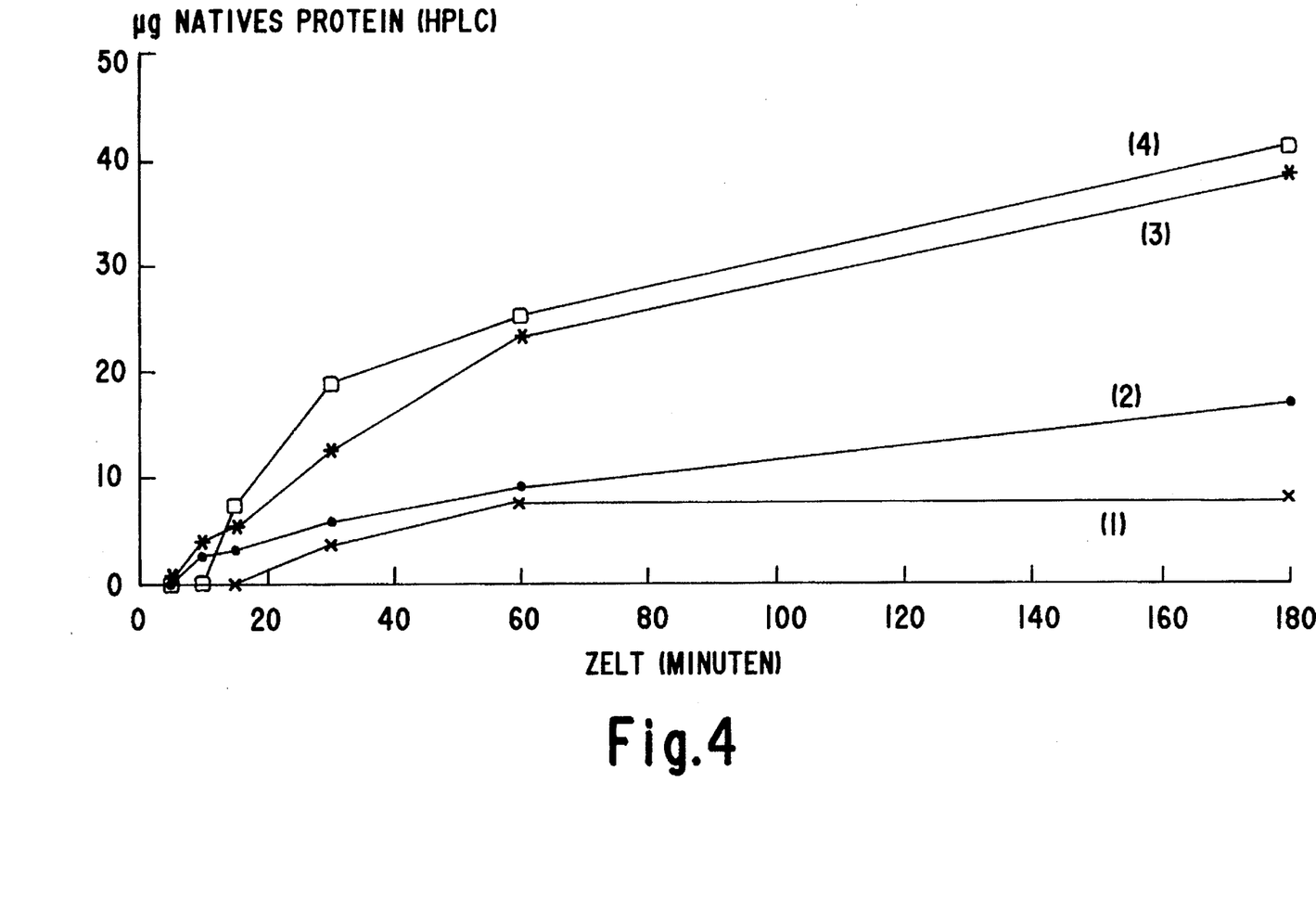
FIG. 4 shows the reactivation yield in relation to the incubation time (arginine concentration 0.2 mol/l, curve nomenclature is analogous to FIGS. 1 and 2).

FIG. 4 shows the dependence of the reactivation yield on the incubation period.

---

We claim:

1. Process for improving the renaturation of recombinant proteins, comprising the steps of:

adding at least one oligonucleotide sequence encoding a helper sequence of 2 to 20 amino acids in length to a DNA sequence coding for a protein, wherein said oligonucleotide sequence is added to the part of the DNA sequence encoding the protein's N and/or C-terminus, and wherein the relative hydrophobicity of said helper sequence, calculated as the sum of the relative hydrophobicities for the individual amino acids, is a negative numerical value, and wherein the helper sequences have a value for the ratio of relative hydrophobicity to the number of amino acids which is −2.0 kcal/mol or less, expressing the DNA sequence including the oligonucleotide sequence encoding said helper sequence, and thereafter renaturing any expressed protein.

2. Process according to claim 1, wherein the helper sequences have a value for the ratio of relative hydrophobicity to the number of amino acids which is −2.5 kcal/mol or less.

3. Process according to claim 1, wherein the oligonucleotide sequence is added to the part of the DNA sequence coding for the N-terminus of the recombinant protein.

4. Process according to claim 1, wherein the oligonucleotide sequence is added to the part of the DNA sequence coding for the C-terminus of the recombinant protein.

5. Process according to claim 1, wherein the helper sequences contain at least two amino acids selected from the group consisting of glutamate, aspartate, lysine, arginine and proline.

6. Process according to claim 5, wherein the helper sequences contain at least two glutamate residues.

7. Process according to claim 5, wherein the helper sequences contain two successive amino acids having the same charge selected from the group consisting of glutamate, aspartate, lysine and arginine.

8. Process according to claim 7, wherein the helper sequences contain two successive glutamate residues.

9. Process according to claim 1, further comprising the addition of a DNA fragment encoding a cleavage site between the oligonucleotide sequence encoding the helper sequence and the DNA encoding the protein.

10. Process according to claim 9, wherein the cleavage site is a sequence recognized by a protease.

11. Process according to claim 10, wherein the cleavage site is an IgA protease cleavage site.

12. Process according to claim 11, wherein the cleavage site is a factor Xa cleavage site.

13. Process according to claim 1, wherein the helper sequence is selected from the group consisting of:

Met-Glu (SEQ ID:1)

Met-Thr-Pro-Leu-Pro-Arg-Pro-Pro (SEQ ID NO: 2)

Met-Thr-Pro-Leu-His-His-Pro-Arg-Pro-Pro (SEQ ID NO: 3)

Met-Thr-Pro-Leu-Lys-Lys-Pro-Arg-Pro-Pro (SEQ ID NO: 4)

Met-Thr-Pro-Leu-Glu-Glu-Gly-Pro-Arg-Pro-Pro (SEQ ID NO: 5)

Met-Thr-Pro-Leu-Glu-Glu-Gly-Thr-Pro-Leu-Pro-Arg-Pro-Pro (SEQ ID NO: 6)

Met-Thr-Pro-Leu-Glu-Glu-Gln-Pro-Pro (SEQ ID NO: 7)

Met-Lys-Ala-Lys-Arg-Phe-Lys-Lys-His-Pro-Arg-Pro-Pro (SEQ ID NO: 8)

Met-Thr-Pro-Leu-Glu-Glu-Gly-Ile-Glu-Gly-Arg (SEQ ID NO: 9) and

Met-Thr-Pro-Leu-Lys-Ala-Lys-Arg-Phe-Lys-His-Pro-Arg-Pro-Pro (SEQ ID NO: 10).

14. The process according to claim 1, wherein said protein is selected from the group consisting of granulocyte colony stimulating factor (G-CSF) and a granulocyte stimulating factor (G-CSF) mutein, wherein one or more amino acids selected from the group consisting of (i) the amino acids of the sequence His-Ser-Leu at positions 52–54 of the mature G-CSF with 174 amino acids, (ii) the amino acids of the sequence His-Ser-Leu at positions 55–57 of the mature G-CSF with 177 amino acids, (iii) the His residues at positions 43, 79, 156 or 170 of the mature G-CSF with 174 amino acids and (iv) the His residues at positions 46, 82, 159 or 173 of the mature G-CSF with 177 amino acids are substituted with a different amino acid or deleted in said mutein.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
      ( A ) LENGTH: 2 amino acids
      ( B ) TYPE: amino acid
      ( D ) TOPOLOGY: linear    ( x i ) SEQUENCE DESCRIPTION: SEQ ID NO:1:

Met Glu
   1

( 2 ) INFORMATION FOR SEQ ID NO:2:

( i ) SEQUENCE CHARACTERISTICS:
      ( A ) LENGTH: 8 amino acids
      ( B ) TYPE: amino acid
      ( D ) TOPOLOGY: linear    ( x i ) SEQUENCE DESCRIPTION: SEQ ID NO:2:

Met Thr Pro Leu Pro Arg Pro Pro
   1                     5

( 2 ) INFORMATION FOR SEQ ID NO:3:

( i ) SEQUENCE CHARACTERISTICS:
      ( A ) LENGTH: 10 amino acids
      ( B ) TYPE: amino acid
      ( D ) TOPOLOGY: linear    ( x i ) SEQUENCE DESCRIPTION: SEQ ID NO:3:

Met Thr Pro Leu His His Pro Arg Pro Pro
   1                     5                         10

( 2 ) INFORMATION FOR SEQ ID NO:4:

( i ) SEQUENCE CHARACTERISTICS:
      ( A ) LENGTH: 10 amino acids
      ( B ) TYPE: amino acid
      ( D ) TOPOLOGY: linear    ( x i ) SEQUENCE DESCRIPTION: SEQ ID NO:4:

Met Thr Pro Leu Lys Lys Pro Arg Pro Pro
   1                     5                         10

( 2 ) INFORMATION FOR SEQ ID NO:5:

( i ) SEQUENCE CHARACTERISTICS:
      ( A ) LENGTH: 11 amino acids
      ( B ) TYPE: amino acid
      ( D ) TOPOLOGY: linear    ( x i ) SEQUENCE DESCRIPTION: SEQ ID NO:5:

Met Thr Pro Leu Glu Glu Gly Pro Arg Pro Pro
   1                     5                         10

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( D ) TOPOLOGY: linear     ( x i ) SEQUENCE DESCRIPTION: SEQ ID NO:6:

```
Met Thr Pro Leu Glu Glu Gly Thr Pro Leu Pro Arg Pro Pro
1               5                   10
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( D ) TOPOLOGY: linear     ( x i ) SEQUENCE DESCRIPTION: SEQ ID NO:7:

```
Met Thr Pro Leu Glu Glu Gln Pro Pro
1               5
```

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( D ) TOPOLOGY: linear     ( x i ) SEQUENCE DESCRIPTION: SEQ ID NO:8:

```
Met Lys Ala Lys Arg Phe Lys Lys His Pro Arg Pro Pro
1               5                   10
```

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( D ) TOPOLOGY: linear     ( x i ) SEQUENCE DESCRIPTION: SEQ ID NO:9:

```
Met Thr Pro Leu Glu Glu Gly Ile Glu Gly Arg
1               5                   10
```

( 2 ) INFORMATION FOR SEQ ID NO:10:

( i ) SEQUENCE CHARACTERISTICS:
        ( A ) LENGTH: 16 amino acids
        ( B ) TYPE: amino acid
        ( D ) TOPOLOGY: linear     ( x i ) SEQUENCE DESCRIPTION: SEQ ID NO:10:

```
Met Thr Pro Leu Lys Ala Lys Arg Phe Lys Lys His Pro Arg Pro Pro
1               5                   10                  15
```

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

```
AATTCGGAGG AAAAATTA                                              18
```

( 2 ) INFORMATION FOR SEQ ID NO:12:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

ACACCACTGG GCC  13